United States Patent [19]

Lien

[11] Patent Number: 5,511,539

[45] Date of Patent: Apr. 30, 1996

[54] DOSE INHALER

[76] Inventor: Su-chu Lien, 5F, 200 Min-chu Rd., Lu-chou Hsiang, Taipei Hsien, Taiwan

[21] Appl. No.: 492,161

[22] Filed: Jun. 19, 1995

[51] Int. Cl.$^6$ ............................................. A61M 11/00
[52] U.S. Cl. ............................. 128/200.21; 128/200.14; 128/200.16; 128/204.14
[58] Field of Search ..................... 128/200.21, 200.16, 128/200.18, 200.14, 204.14, 203.16, 203.17, 203.25, 203.26, 203.27; 239/102.2

[56] References Cited

U.S. PATENT DOCUMENTS

| 478,896 | 7/1892 | Underwood | 128/203.26 |
|---|---|---|---|
| 3,746,000 | 7/1973 | Edwards | 128/200.16 |
| 4,036,919 | 7/1977 | Komendowski et al. | 128/200.18 |
| 5,080,093 | 1/1992 | Raabe et al. | 128/200.21 |
| 5,361,989 | 11/1994 | Merchat et al. | 239/102.2 |

FOREIGN PATENT DOCUMENTS

| 5123400 | 5/1993 | Japan | 128/200.16 |
|---|---|---|---|

*Primary Examiner*—Edgar S. Burr
*Assistant Examiner*—V. Srivastava
*Attorney, Agent, or Firm*—Beveridge, DeGrandi, Weilacher & Young

[57] ABSTRACT

An improvement to dose inhaler comprises a cover lid, a channel lid, a water chamber, a power set and a bottom. Characterized in that the power set includes a housing, an oscillator and a circuit. The housing which is disposed with the circuit is installed at the bottom. An oscillator is electrically interconnected with the circuit. The water chamber is disposed above the oscillator and is used to contain water use to mix with medicine. One side of the water chamber is provided with a channel. A channel lid includes a retaining port and an air channel which has an inhaling port at one side. The retaining port is disposed right above the water chamber. A cup for medicine is disposed above the retaining port. One side of the medicine cup is provided with an inhaling port. Consequently, a passage is defined by the channels and is intercommunicated with the inhaling port. Besides, the transient surface between the retaining port and the top of the air channel is configured with an inclination toward the retaining port. The cover lid is provided with an opening with respect to the retaining port of the channel lid. A transparent lid is provided at the opening.

1 Claim, 3 Drawing Sheets

DOSE INHALER

BACKGROUND OF THE INVENTION

This invention relates to a dose inhaler, more particularly to an improvement of a dose inhaler powered which features an isolated chamber for dose of medicine and water in order to prevent the mixing of the dose and water during the operation. Accordingly, the dose is reserved economically.

The conventional supersonic dose inhaler generally includes a chamber and an oscillator. The dose of medicine and water are contained within the chamber and an oscillator is disposed at the bottom of the chamber. The oscillator provides an oscillation via electo-mechanic configuration, consequently, the water is vaporized and mixed with medicine by the operation of said oscillation to form a stream. One side of the chamber is provided with a port and interconnected with a pipe thereof. By this arrangement, the stream is capable of being directed into the respiratory system through the nostril or mouth. In the conventional configuration, the chamber shall be contained with water not only to facilitate the operation, but also because the water may prevent the oscillator from malfunctioning as a result of continuous operation without water. On the other hand, this may also prevent the patient from inhaling intensified medicine. But once the medicine is mixed with water, both the medicine and water will be spoiled after a period of time. On the other hand, the medicine will vaporize with the water.

Besides, the chamber is provided with an enclosed space serving the vaporized medicine. The enclosed space is integral with the chamber and can not disassembled. It is difficult and impossible for the user to recognize whether the medicine has run out or not, an inconvenience to the user. On the other hand, the vaporized medicine may form a scale attached to the inner wall of the chamber. It may cause a great cleaning problem to the enclosed space because the enclosed space provides no access.

SUMMARY OF THE INVENTION

It is the object of this invention to provide an improvement of a dose inhaler powered which features an isolated chamber for water and medicine. Accordingly, the medicine is prevented from vaporizing with water both before and after operation. Consequently, the medicine is saved and the oscillator is secured from malfunctioning resulting from endless operation without water.

It is still the object of this invention to provide an improvement of a dose inhaler wherein the inhaler can be readily cleaned.

In order to achieve the object set forth, the dose inhaler comprises a cover lid, a channel lid, a water chamber, a power set and a bottom, characterized in that the power set includes a housing, an oscillator and a circuit. The housing which is disposed with the circuit is installed at the bottom. An oscillator is electrically interconnected with the circuit. The water chamber is disposed above the oscillator and is used to contain water used to mix with the medicine. One side of the water chamber is provided with a channel. A channel lid includes a retaining port and an air channel which has an inhaling port at one side. The retaining port is disposed right above the water chamber. A cup for medicine is disposed above the retaining port. One side of the medicine cup is provided with an inhaling port. Consequently, a passage is defined by the channels and is intercommunicated with the inhaling port. Besides, the transient surface between the retaining port and the top of the air channel is configured with an inclination toward the retaining port. The cover lid is provided with an opening with respect to the retaining port of the channel lid. A transparent lid is provided at the opening.

BRIEF DESCRIPTION OF THE DRAWINGS

The structural and operational characteristics of the present invention and its advantages as compared to the known state of the prior art will be better understood from the following description, in conjunction with the attached drawings which show illustratively but not restrictively an example of an improvement to a dose inhaler powered. In the drawings.

DETAILED DESCRIPTION OF PREFERRED EMBODIMENT

Figure 1:
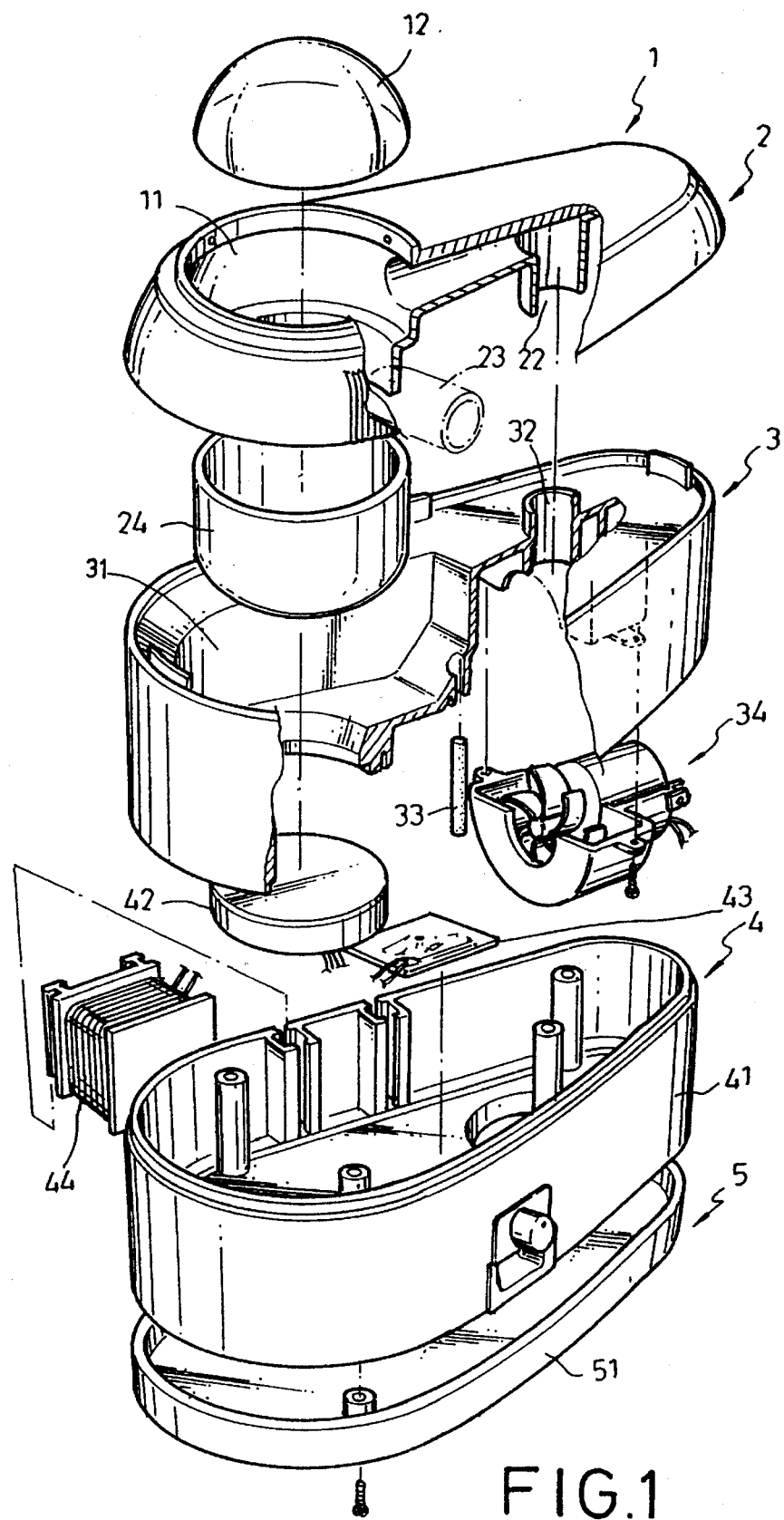
FIG. 1 is an exploded perspective view of the dose inhaler made according to this invention.
Figure 2:
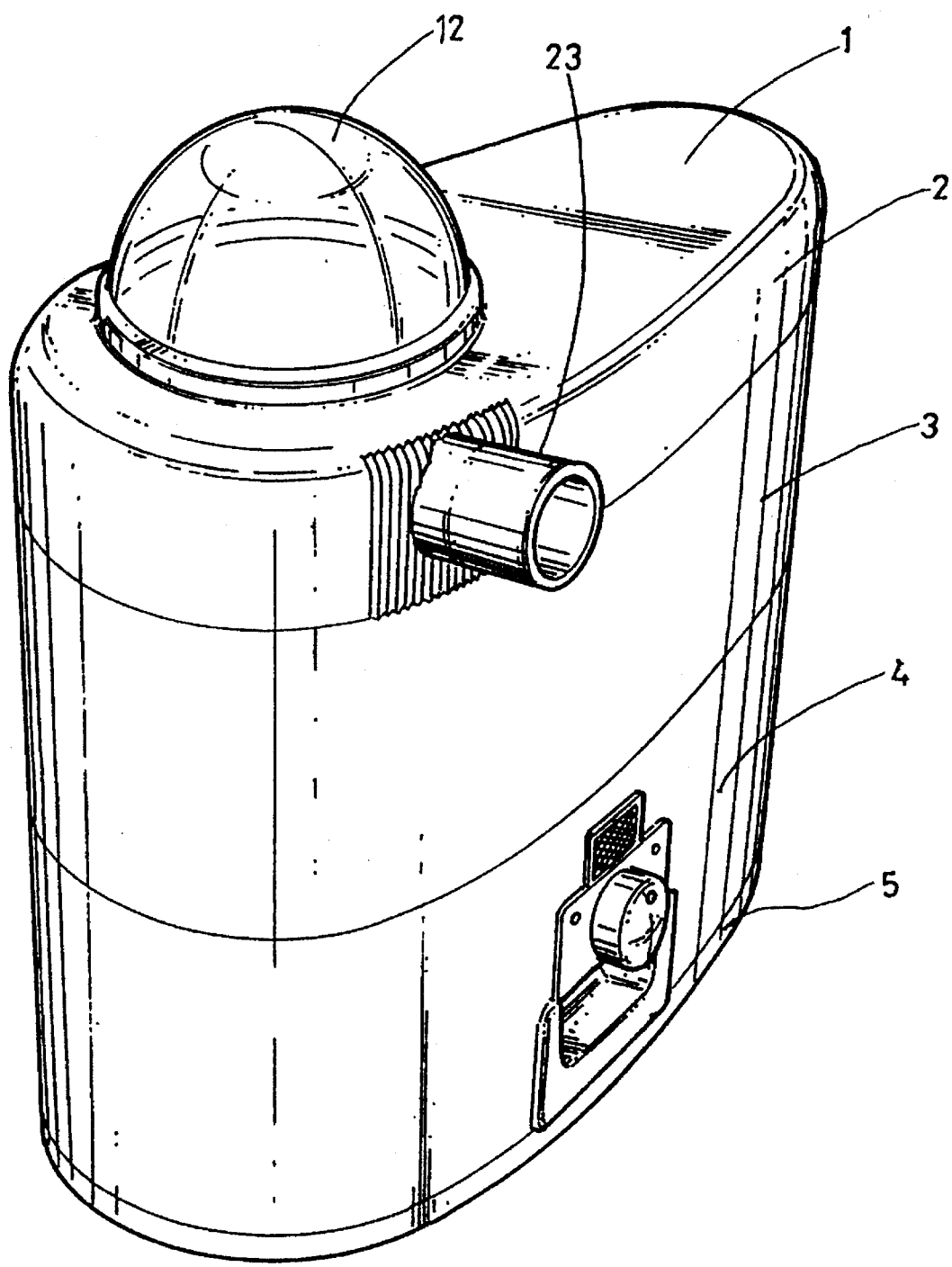
FIG. 2 is a sketch view showing the assembled dose inhaler with the elements disclosed in FIG. 1.

Referring to FIGS. 1 and 2, the dose inhaler comprises a cover lid 1, a channel lid 2, a water chamber 3, a power set 4 and a bottom 5. Each of the elements is configured with mating device, for example, a bayonet configuration, for inter-connection therebetween. By orderly attachment, the dose inhaler is assembled.

Figure 3:
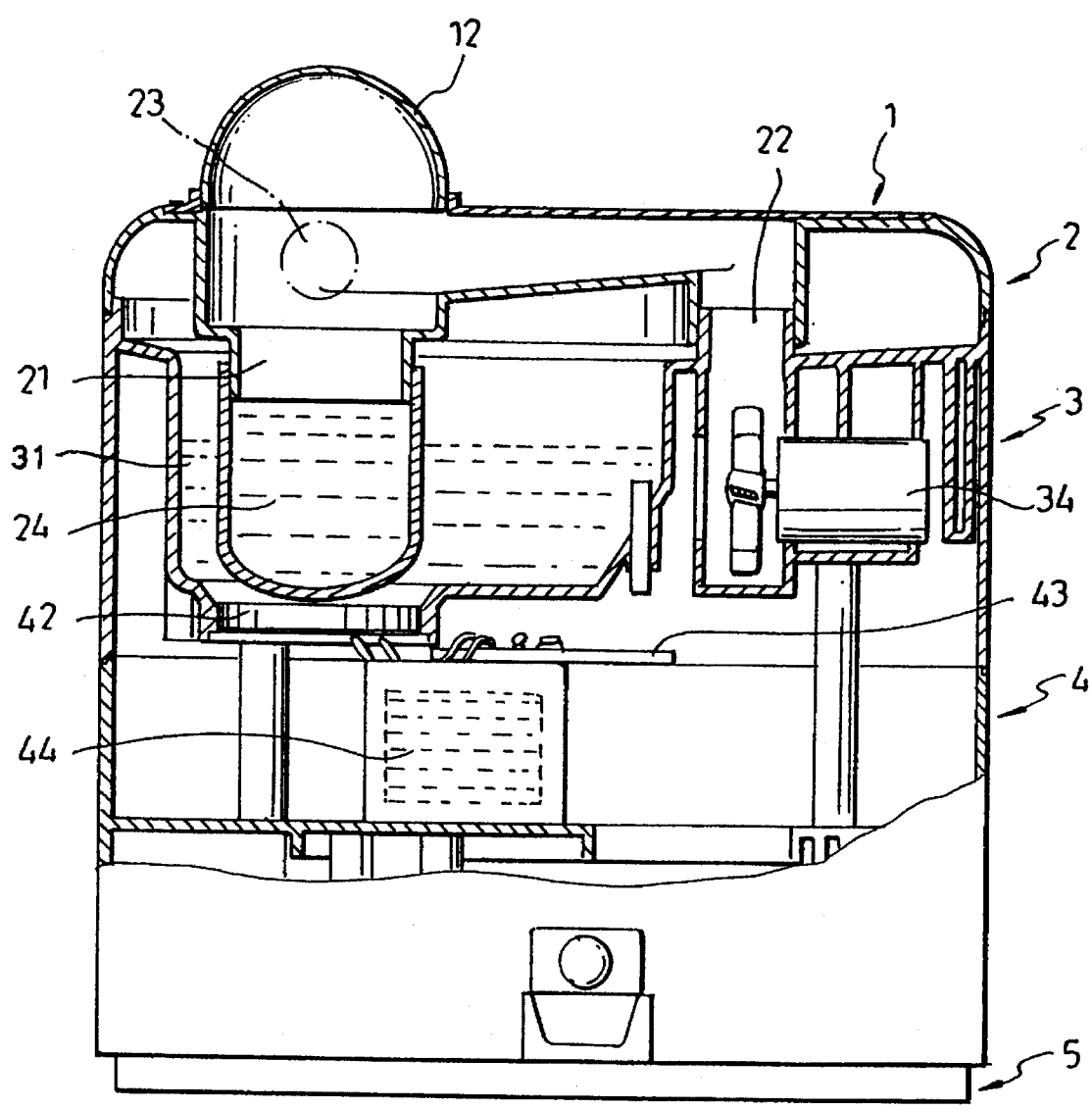
FIG. 3 is a cross sectional view of the dose inhaler made according to this invention.

Referring to FIGS. 1 and 3, the bottom 5 is provided with a projected wall 51 at the peripheral. The power set 4 includes a housing 41, an oscillator 42 and a circuit 43. The housing 4 is interconnected with the projected wall 51 of the bottom 5. The circuit 43 together with the oscillator 43 are disposed within the housing 41. A transformer 44 is electrically connected with the oscillator 42. The water chamber 3 includes a chamber 31 for containing water. The bottom of the water chamber 3 is right above the oscillator 42 of the power set 4. One side of the chamber 31 is provided with an air channel 32 and a fan 34 is disposed right below the air channel 32. A level sensor 33 is provided within the chamber 31. The level sensor 33 may actuate an alarm and cut off the power supply of the oscillator 42 when the water level is lowered to a predetermined level. The level sensor 33 is a conventional device which is affordable in the market. The channel lid 2 is provided with a retaining port 21 and an air channel 22. An inhaling port 23 is provided at the side of the channel lid 2. The inhaling port 23 is right above the chamber 31 of the water chamber 3. A medicine cup 24 is disposed above the retaining port 21. The inhaling port 23 is above the medicine cup 24. A passage is defined by the channels 22 and 32 of the water chamber 3 and eventually interconnected with the inhaling port 23. On the other hand, the transient surface between the retaining port 21 and the top of the air channel 22 is configured with an inclination toward the retaining port 21. The cover lid 1 is provided with an opening 11. The opening 11 is disposed right above the retaining port 21 and a transparent plastic lid 12 is disposed thereof.

By the combination of the elements, a dose inhaler is configured. In operation, the medicine cup 24 contains medical liquid and the oscillator 42 is operating as it is switched on. By this arrangement, the patient can direct the inhaling port 23 of the channel lid 2 with its mouth to inhale the vaporized mixture of water and medical liquid to cure his/her throat. When the patient breathes out the air, the ambient air may flow into the channel lid 2 to cause the medical liquid flow into the water chamber 23 through the air channel 22. In order to prevent this, the transient surface between the retaining port 21 and the air channel 22 of the channel lid 2 is made in an inclined way. By this arrangement, the condensed medical liquid may readily flow back to the medical cup 24. On the other hand, the water and the medical liquid are contained separately in medical cup 24 and said chamber 31 of the water chamber 3. Accordingly, the medical liquid and water will not interfere with each other. The quality will not be influenced and/or spoiled.

Because the cover lid 1 and the channel lid 2 are removable, the deposit attached at the inner wall of the channel lid 2 can be readily removed. The channel lid 2 can be readily cleaned after the cover lid 1 is removed. On the other hand, the level sensor 33 is disposed at side of the bottom of the chamber 33 of the water chamber 3. Accordingly, when the water chamber 3 is cleaned, the level sensor 33 will not impart a negative influence to the water chamber 3.

Although the present invention has been described in connection with the preferred embodiment thereof, many other variations and modifications will now become apparent to those skilled in the art without departing from the scope of the invention. It is preferred, therefore, that the present invention not be limited by the specific disclosure herein, but only by the appended claim.

I claim:

1. An inhaler comprising a cover lid, a channel lid, a water chamber, a power set and a bottom;

said power set including a housing, an oscillator and a circuit, said housing which is disposed with the circuit being installed at the bottom, said oscillator being electrically interconnected with the circuit;

said water chamber being disposed above the oscillator and being used to contain water for mixing with a medicinal liquid, one side of said water chamber being provided with an air channel, a water level sensor being provided at the bottom of said water chamber;

said channel lid including a retaining port and a second air channel, and also an inhaling port at one side thereof, said retaining port being disposed right above the water chamber, a cup containing the medicinal liquid being disposed above the water chamber with a top portion of said cup being disposed above said retaining port, a passage being defined by said air channels and being intercommunicated with said inhaling port, a transient surface being provided between said retaining port and said second air channel, said transient surface being inclined towards the retaining port for preventing the medicinal liquid from flowing into the water chamber through said air channels; and said cover lid being provided with an opening in alignment with said retaining port of said channel lid, said opening being provided with a transparent lid.

\* \* \* \* \*